(12) United States Patent
Brennan et al.

(10) Patent No.: US 9,529,969 B2
(45) Date of Patent: Dec. 27, 2016

(54) EVENT BASED TRACKING, HEALTH MANAGEMENT, AND PATIENT AND TREATMENT MONITORING SYSTEM

(71) Applicant: RDFISolutions, LLC, Delmar, NY (US)

(72) Inventors: Brianna B. Brennan, Delmar, NY (US); Sylvia J. Rowlands, Albany, NY (US); Heath J. Stein, Clifton Park, NY (US)

(73) Assignee: RDFISOLUTIONS, LLC, Delmar, NY (US)

( * ) Notice: Subject to any disclaimer, the term of this patent is extended or adjusted under 35 U.S.C. 154(b) by 0 days.

(21) Appl. No.: 14/606,619

(22) Filed: Jan. 27, 2015

(65) Prior Publication Data
US 2015/0213197 A1 Jul. 30, 2015

Related U.S. Application Data

(60) Provisional application No. 61/931,893, filed on Jan. 27, 2014.

(51) Int. Cl.
*G06F 19/00* (2011.01)

(52) U.S. Cl.
CPC ......... *G06F 19/322* (2013.01); *G06F 19/3456* (2013.01)

(58) Field of Classification Search
CPC .................................................. G06F 19/322
USPC ............................ 235/375; 700/86; 709/204
See application file for complete search history.

(56) References Cited

U.S. PATENT DOCUMENTS

| | | | |
|---|---|---|---|
| 8,112,100 B2 | 2/2012 | Frank | |
| 8,340,792 B2 | 12/2012 | Condurso | |
| 8,392,204 B2 | 3/2013 | Camp | |
| 2003/0009244 A1* | 1/2003 | Engleson | G06Q 50/22 700/86 |
| 2007/0299776 A1 | 12/2007 | Frustaci | |
| 2009/0280468 A1 | 11/2009 | Yaskin | |
| 2010/0125932 A1 | 5/2010 | Halk | |
| 2010/0324936 A1 | 12/2010 | Vishnubhatla | |

(Continued)

OTHER PUBLICATIONS

College Uses QR Codes to Improve GPAs; The BarCode News; Jan. 3, 2014; http://barcode.com/201312251873/improving-the-gpas-of-at-risk-students.

*Primary Examiner* — Allyson Trail
(74) *Attorney, Agent, or Firm* — Bond Schoeneck & King, PLLC; George McGuire; Frederick Price

(57) ABSTRACT

The present invention relates to an event based tracking, health management, and patient and treatment monitoring system, and, more particularly, to an event based tracking, health management, and patient and treatment monitoring software system including a unique/custom scanable code (e.g., a quick-response ("QR") code) created for a specific positive/negative event which is tied to at least one specific phone number or other unique identifier of a mobile device, and a software application stored on the mobile device which enables the mobile device to (i) scan the unique QR code (on a card or other item), and (ii) log QR code data indicating the completion (positive) or non-completion (negative) of the event (and related information) in real time into a particular profile in a database (e.g., in a cloud server) for event validation and authentication, health management, and/or patient and treatment monitoring, and for reporting the QR code data (and related information) to authorized clients.

16 Claims, 9 Drawing Sheets

(56) References Cited

U.S. PATENT DOCUMENTS

2011/0175724 A1 7/2011 Kent
2012/0143952 A1* 6/2012 von Graf ............... G06Q 50/01
 709/204

* cited by examiner

FIG. 5B

| CLIENT ID | CLIENT NAME | RX | DATE | TIME | STATUS |
|---|---|---|---|---|---|
| 10 | JOHN DOE | RX20 mg Oxy | 5/6/2013 | 1:30PM | COMPLETE |
| 10 | JOHN DOE | RX20 mg Oxy | 5/7/2013 | 12:33PM | COMPLETE |
| 10 | JOHN DOE | RX20 mg Oxy | 5/8/2013 | 1:49PM | COMPLETE |
| 10 | JOHN DOE | RX20 mg Oxy | 5/9/2013 | 11:58PM | COMPLETE |
| 10 | JOHN DOE | RX20 mg Oxy | 5/10/2013 | 12:16PM | COMPLETE |
| 10 | JOHN DOE | RX20 mg Oxy | 5/11/2013 | 5:39PM | OUTSIDE PARAMENTERS |
| 10 | JOHN DOE | RX20 mg Oxy | 5/12/2013 | 3:02PM | OUTSIDE PARAMENTERS |
| 10 | JOHN DOE | RX20 mg Oxy | 5/13/2013 | 3:13PM | OUTSIDE PARAMENTERS |
| 10 | JOHN DOE | RX20 mg Oxy | 5/14/2013 | 2:00PM | MISSED |
| 10 | JOHN DOE | RX20 mg Oxy | 5/15/2013 | 2:45PM | MISSED |
| 10 | JOHN DOE | RX20 mg Oxy | 5/16/2013 | 2:08PM | MISSED |
| 10 | JOHN DOE | RX20 mg Oxy | 5/17/2013 | 2:14PM | OUTSIDE PARAMENTERS |
| 10 | JOHN DOE | RX20 mg Oxy | 5/18/2013 | 1:24PM | COMPLETE |
| 10 | JOHN DOE | RX20 mg Oxy | 5/19/2013 | 2:39PM | OUTSIDE PARAMENTERS |

FIG. 7

EVENT BASED TRACKING, HEALTH MANAGEMENT, AND PATIENT AND TREATMENT MONITORING SYSTEM

RELATED APPLICATION DATA

The present application claims the benefit of U.S. provisional patent application No. 61/931,893, filed Jan. 27, 2014, and is hereby incorporated by reference in its entirety.

BACKGROUND OF THE INVENTION

1. Field of the Invention

The present invention relates to an event based tracking, health management, and patient and treatment monitoring system, and, more particularly, to an event based tracking, health management, and patient and treatment monitoring software system including a unique/custom scanable code (e.g., a quick-response ("QR") code) created for a specific positive/negative event which is tied to at least one specific phone number or other unique identifier of a mobile device, and a software application stored on the mobile device which enables the mobile device to (i) scan the unique QR code (on a card or other item), and (ii) log QR code data indicating the completion (positive) or non-completion (negative) of the event (and related information) in real time into a particular profile in a database (e.g., in a cloud server) for event validation and authentication, health management, and/or patient and treatment monitoring, and for reporting the QR code data (and related information) to authorized clients.

2. Description of the Related Art

Conventional event based tracking, health management, and/or patient and treatment monitoring systems can be categorized into three groups: mHealth technology platforms, Management Information Systems (MIS), and Electronic health Records (EHR's).

mHealth technology platforms are coarsely categorized into two groups—1) medical and health, and 2) wellness. Physicians using mHealth technology are not necessarily able to connect these technologies to their practice or hospital.

MIS: Case management solutions are often bulky, difficult to navigate and take a great deal of customizing to be effective in the behavioral health industries. Case management solution typically lack functionality outside of having the framework for data collection and storage. Although case management solutions are widely used in health services, there are few that are tailored to fit the needs of the majority of behavioral health and child welfare treatments. Additionally, all case management solutions require timely manual data entry from care providers to update and report on treatment events.

The purpose of EHR integration into the health care industry is to increase accessibility and streamline exchange of patient information. An EHR is more than just a computerized version of a paper chart; it's a digital record that provides a comprehensive health history. EHR systems are built to share information with other health care providers and organizations—such as laboratories, specialists, medical imaging facilities, pharmacies, emergency facilities, as well as school and workplace clinics—as such; EHR's contain information from all clinicians involved in a patient's care. EHR's will be tasked to centralize all patent information to a conglomerate depot. However, due to the "general design" of these systems few bridge the gap between health and behavioral health services. Like other treatment management systems EHR's require timely manual data entry to update client records. Additionally, these systems are not mandated to provide necessary data analysis and outcomes reporting and will require an increase in administrative tasks such as tracking patient activity, treatment compliance and updating patient treatment information.

Conventional event-based tracking systems, health management and/or patient and treatment monitoring systems also require a manual entry approach for tracking on treatment events and often call upon memory, review of notes, and in some cases, third-party reports. The results of standard practice (manually logging) can be key stroke errors, delays in updated reports and reporting bias.

Set forth below is an example of standard practice in treatment event-monitoring in the behavioral health field: In some practices, i.e. child-welfare; certain treatment event details are reported by third-party participants to a treatment staff members and at that point the event details are manually reported. In the scenario of school attendance in some jurisdictions, for example, school staff must complete a handwritten "attendance card" and submit this to agency staff. Additionally, in some scenarios, agency staff must manually contact the client's school directly and speak with staff regarding a child's attendance. In all scenarios, every data point that is required by the model proprietor must be manually logged either into an electronic database or completed in triplicate and submitted for compliance review.

Description of the Related Art Section Disclaimer: To the extent that specific publications/systems are discussed above in this Description of the Related Art Section, these discussions should not be taken as an admission that the discussed publications/systems are prior art for patent law purposes. For example, some or all of the discussed publications/systems may not be sufficiently early in time, may not reflect subject matter developed early enough in time and/or may not be sufficiently enabling so as to amount to prior art for patent law purposes. To the extent that specific publications are discussed above in this Description of the Related Art Section (as well as throughout the application), they are all hereby incorporated by reference into this document in their respective entirety(ies).

SUMMARY OF THE INVENTION

Various embodiments of the present invention may be advantageous in that they may solve or reduce one or more of the potential problems and/or disadvantages with conventional event based tracking, health management, and/or patient and treatment monitoring systems discussed above.

Various embodiments of the present invention may exhibit one or more of the following objects, features and/or advantages:

It is therefore a principal object and advantage of the present invention to provide an event based tracking, health management, and patient and treatment monitoring system that tracks real behaviors and collects behavior related and/or clinical data in real time (rather than responding to reported behaviors) allowing responses to behaviors in real time. Stated differently, the system provides real-time, authentic, precise reports with the additional component of real behavior reporting.

It is an additional object and advantage of the present invention to provide an event based tracking, health management, and patient and treatment monitoring system that is structured, configured and/or programmed to create a unique/custom quick-response ("QR") code for a specific positive/negative event, and which is tied to at least one specific phone number or other unique identifier of a mobile device (e.g., smart phone, tablet etc.).

It is a further object and advantage of the present invention to provide an event based tracking, health management, and patient and treatment monitoring system including a mobile device that is structured, configured, and/or programmed to scan a unique QR code (on a card or other item) and log information (indicating the completion (positive) or non-completion (negative) of the event) in real time into a particular profile in a database for event validation and authentication, to support an evidence based treatment program, health management, and/or patient and treatment monitoring. Reporting/alerts can then be created and immediately be transmitted to particular authorized clients.

It is another object and advantage of the present invention to provide an event based tracking, health management, and patient and treatment monitoring system that is interactive by providing various "response" alerts. Alerts can include, but are not limited to, a reminder of an upcoming event, the receipt of a successful positive QR scan, the receipt of a successful negative scan, the receipt of a QR code scan outside the proscribed/associated timeframe, or no QR code scan received within the proscribed/associated date and timeframe.

It is another object and advantage of the present invention to provide an event based tracking, health management, and patient and treatment monitoring system including software applications that include administrative access, point-of-use, real-time alerts of treatment events (as noted above), authentic data of every event, customized reports, and cross database integration.

It is another object and advantage of the present invention to provide an event based tracking, health management, and patient and treatment monitoring system that improves professionalism and quality of work by making documentation automatic, and, thus, allowing treatment providers to pay attention to clients and treatment plans instead of documentation.

It is another object and advantage of the present invention to provide an event based tracking, health management, and patient and treatment monitoring system that allows treatment providers to keep constant with clients.

In accordance with the foregoing objects and advantages, an embodiment of the present invention is directed to an event based tracking, health management, and patient and treatment monitoring system that can include, but is not limited to: a mobile device with a software application stored thereon (i.e., a non-transitory computer-readable storage medium having program code for performing certain functionality) that is structured, configured, and/or programmed to scan a unique QR code (on a card or other item) created specifically for at least the particular mobile device, and for a particular purpose and representing specific data (e.g., indicating the completion (positive) or non-completion (negative) of the event), to validate the QR code, and to securely transmit the QR code and the corresponding specific data from the mobile device (preferably, but not necessarily, in real time) into a particular profile in a database (e.g., in a cloud server which can include a web application) for event validation and authentication, health management, and/or patient and treatment monitoring.

The transmission/transfer of data from the mobile device to the database (or from the database to a user or client device) can be via SMS text, or via wireless communication/transmission over a network, which can be any suitable wired or wireless network capable of transmitting communication, including but not limited to a telephone network, Internet, Intranet, local area network, Ethernet, online communication, offline communications, wireless communications and/or similar communications means, or via default SMS text. The wireless transmission can be accomplished through any wireless protocol/technology, including, but not limited to, ZigBee standards-based protocol, Bluetooth technology, and/or Wi-Fi technology. Further, this data can be encrypted as needed based on the sensitivity of the data or the location the database with respect to the mobile device, for example. The database can be located in the same room, in a different room in the same building, in a completely different building and location from the mobile device, or in the "cloud." The storage of the data in the cloud can be subject to security measures, as should be appreciated by those of skill in the art. Various alerts and notifications can be sent to authorized users of the system from the database via SMS text, for example, or any other data transmission means.

The use of the event based tracking and health management software application and system can be in Evidence Based Treatment ("EBT"), in health management (including behavioral and health treatment), and in home-health, addiction recovery, medication therapy management, behavioral health etc. where the client supports remote patient monitoring.

BRIEF DESCRIPTION OF THE DRAWINGS

The present invention will be more fully understood and appreciated by reading the following Detailed Description in conjunction with the accompanying drawings, in which:

FIGS. 5A-C each show an example user interface showing an event creation functionality of the event based tracking, health management, and patient and treatment monitoring system, according to an embodiment of the present invention.

FIG. 7 is an illustration of a report that can be generated regarding a series of events and their relative completion indicators, according to an embodiment of the present invention.

DETAILED DESCRIPTION

Figure 1:
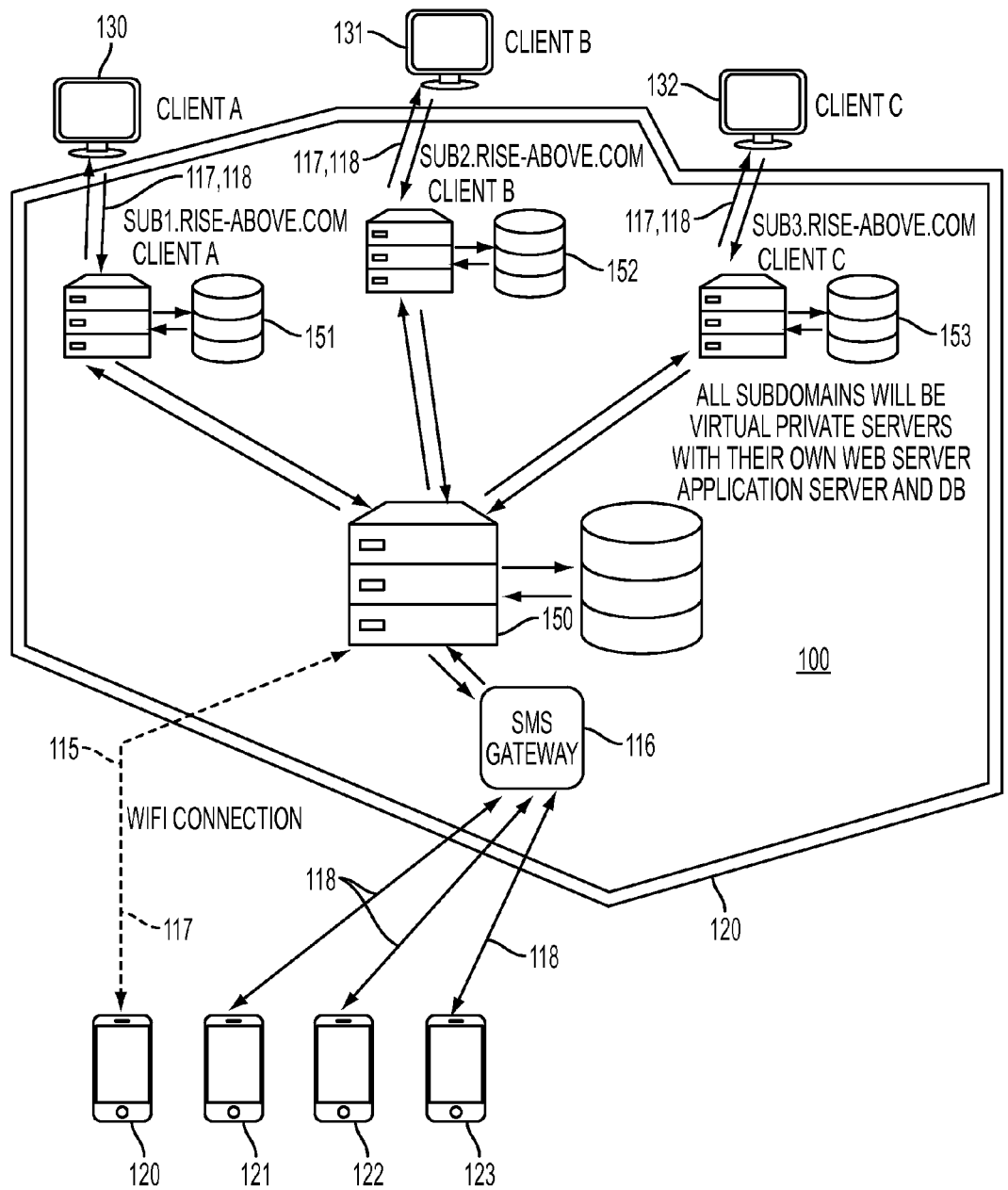
FIG. 1 is a system architecture diagram of an event based tracking, health management, and patient and treatment monitoring system with various communication links, according to an embodiment of the present invention.

The present invention will be more fully understood and appreciated by reading the following Detailed Description in conjunction with the accompanying drawings, wherein like reference numerals refer to like components.

Embodiments of the present invention comprise an event based tracking, health management, and patient and treatment monitoring system, and methods for using the same. More specifically, embodiments of the present invention comprise a combination of a consumer facing mobile application that works in sync with a cloud-based web application. For purposes of clarification "QR code data" or "treatment data" is any data/information related to an event being tracked and monitored by the system. The mobile device is enabled by the mobile application to use scanning technology to read and send encrypted treatment data reporting the successful (scan positive QR code specific for the event and the mobile device) or unsuccessful (scan negative QR code specific for the event and mobile device) results of any treatment event that is being tracked and monitored. The treatment data is uploaded in real time to a database module in the web application while simultaneously sending a text message to treatment team/support network clients confirming the result of the treatment event.

A single function mobile application is provided and designed to be installed on a mobile device, which is designed to enable the mobile device to perform scanning of custom QR codes specifically created to be scanned by the mobile device (and where the mobile device is specifically enabled to scan the custom QR code). Once a scan is preformed and the QR code is validated as needed, notification can be securely sent (via SMS/WiFi) to all treatment providers and support networks, additionally, scan validations can be stored on the cloud server and database.

The system includes a web browser that allows the treatment team access to a patient's (client's) use of the mobile application (successful scans, unsuccessful scans and not scanned within time perimeter). Browsers can comprise a user interface that can be designed to enable user and client devices (described below) to access, retrieve, and view resources and documents stored in the network, including resources and documents found on the Internet or an Intranet, and locally-stored files, among other sources. For example, the browser can be designed for viewing an Intranet within an organization, or any other connection of local computers. All data can be stored in the network for use by treatment teams, purveyors and agencies etc. The web browser additionally acts as the utility for which treatment teams manage (create/delete/modify) QR codes. QR codes can be created in correlation to any actionable treatment event (i.e. medication management, attendance, therapy sessions, behavioral supports, curfew etc.).

The backend of the system can preferably be a MySQL database and the application server language .net JavaScript can be the script language that is part of a webpage, the front-end can preferably be HTML5 (Html 5 is a mix of html/css3 and JavaScript) and the API can be built in ASP.Net.

The mobile device application (e.g., cell phone app) can be optimized for Android™ operating systems or other mobile device operating systems including iOS. An embodiment of the mobile application is unique in that it is backward compatible to fit the most primitive first generation Android™ phones. A preferable embodiment was built this way, in part, because the mobile application can be used in health self-management for clients receiving treatment. Information transmitted via mobile device can utilize a default WIFI system and an automatic back-up Short Message Service (SMS) gateway. This design was employed for two main reasons: (1) to ensure that the largest percent of the market including rural areas that do not have access to WIFI could be reached, and (2) using WIFI requires a data package that can be expensive, whereas, text messaging plans are typically inexpensive and standard on phones and are available to users on government assisted phone plans.

The system of an embodiment of the present invention is a cloud-based solution that allows for direct and immediate access to records via web browser. Each agency and treatment provider (i.e., client) can have their own unique servers (virtual or otherwise) and web portal. This means that each client can have their own supported web application. There are many benefits to such a cloud-based solution including, in a preferable embodiment: (1) there is no additional hardware to purchase or software to download; (2) the cloud system is available in real-time from any location with internet access; and (3) due to the systemic structure of a cloud server, little to no "down time" is experienced by users.

A web application is provided that can have 3 main modules including: (1) the dashboard module which is configured and/or programmed to manage the addition and removal of patients in treatment as well as manage demographic information such as birthdate, time in treatment, emergency contacts, address and patient ID; (2) the data collection module which is configured and/or programmed to create, update, and delete custom QR codes for tracking treatment events; and (3) the reports module which is configured and/or programmed to manage all the treatment events that are scanned and tracked with precise time and date stamp. The reports module can be customized to meet the reporting requirements of a client such as: court reports, medication compliance, treatment event tracking, API connection into pre-existing database, and third party billing or EHR's.

Advantages of the invention are illustrated by the following Exemplary System, Uses and Functionalities description. However, the particular components, uses, functionalities and amounts thereof recited in this description, as well as other conditions and details, are to be interpreted to apply broadly in the art and should not be construed to unduly restrict or limit the invention in any way.

Exemplary System, Uses, and Functionalities

Turning to FIG. 1, a system architecture diagram of an event based tracking, health management, and patient and treatment monitoring system with various communication links is shown, according to one embodiment of the present invention. A network system 100, a plurality of user devices 120-123, and a plurality of client devices 130-132 can communicate with one another over a network 115 through a communication gateway (not shown). Network 115 can be any suitable wired or wireless network capable of transmitting communication, including but not limited to a telephone network, Internet, Intranet, local area network, Ethernet, online communication, offline communications, wireless communications and/or similar communications means. The network 115 can comprise one or more servers (not shown) to facilitate the communication. The server can be any processor, server, mainframe computer, or other processor-based device capable of facilitating communication. Alternatively, data communication can be via SMS text 118 through a SMS gateway 116.

User devices 120-123 are preferably any mobile device (e.g., smart phone, tablet etc.) comprising a processor and preferably a network connection and capable of running, mirroring, displaying, or otherwise interacting with the software application (preferably stored thereon, but does not have to be) related to the event based tracking, health management, and patient and treatment monitoring system, and communicating with the host system 100.

Examples of client devices 130-132 include personal computers, desktops, laptops, tablets, as well as any other fixed or mobile computerized device comprising a processor and a network connection and capable of communicating with the host system 100. The client devices 130-132, therefore, can be any processor-based device that are capable of facilitating the user's access and interaction with the host system 100. The client devices 130-132 can also comprise or be associated with a dedicated or shared database.

The processors of the user and client devices can comprise or are in communication with the non-transitory computer-readable medium on which is stored computer-executable program instructions that are executed by the processor to cause the processor to perform one or more of the functionalities and/or method step described herein. In an alternative embodiment, a processor that works with a particular user or client device can be located remotely instead of locally, and can be in wired or wireless communication.

The network 100 can include a master server and database 150 (which can include the web application described herein, and which can include more than one server and database), and sub-virtual private servers and databases 151-153. Each client device 130-132 can have access only to a specific sub-virtual private server and database 151-153 as shown, unless a permission is granted to gain access to an additional sub-virtual private server and database. Additional master servers and databases, sub-virtual private servers and databases, user devices and client devices are contemplated.

A brief discussion of the use of the event based tracking, health management, and patient and treatment monitoring system of an embodiment of the present invention will now be described. In accordance with one embodiment, a card (or other physical component—e.g., medication bottle) with a QR code can be held by a patient/client/consumer in the case where the patient's/client's/consumer's attendance or probation—"check-in" or "check-out" of home group therapy—for example, needs to be tracked (i.e., a positive/negative event). In accordance with another embodiment, where a caseworker needs to track curfew, medication, or participates in a home visitation of a patient/client, then the caseworker can be in control of the card. Stated differently, the QR code "card holder" can be the person responsible for delivering the results of a positive/negative treatment event. This means a client, teacher, probation officer, caseworker can all be responsible for delivering the results of certain treatment events—the way the codes are managed can be at the discretion of the design of the evidence based treatment—each treatment describes its own implementation and each can be different. To that respect, each EBT can be developed to gather different info and have different parties in the treatment process responsible for different event reports.

When the patient is required to receive medication or treatment, or is required to attend school as the identified treatment, for example, a specific and encrypted QR code for school attendance on a per class basis can be created by the web application of an embodiment of the present invention. The creation of a QR code is completed by accessing the secure, cloud-based web browser (as discussed above). See FIGS. 5A-5C (and related discussion below) regarding an illustration of an example user interface showing an event creation functionality of the event based tracking, health management, and patient and treatment monitoring system, and the creation of a unique customized QR code associated therewith according to an embodiment of the present invention.

In the school/class attendance example, the patient can present the QR code, which is preferably on a card, to the teacher every time the patient is present at each class during the school day. The teacher can use his/her mobile device (user device 120-123) enabled by the mobile app stored thereon to scan the QR code on the card, which transmits data via a wireless connection 117 or via SMS text 118 through firewall 120 to the network 100 and to the database 150. The QR code data is logged into the patient's unique profile in a specific sub-virtual private server and database 151-153 (preferably in real time) for event validation and authenticating. This QR code data (and any information related thereto) can then immediately be transmitted as a client alert to the respective client device 130-132 associated with the particular sub-virtual private server and database 151-153 and with a security permission to view and obtain such QR code data. This transmission of data can be from the network 100 and particular sub-virtual private server and database 151-153 (or master server and database 150) through firewall 120 via a wireless connection 117 or via SMS text 118.

In particular, if the patient does not report to class then a negative validation can be reported in the system and the CP/Primary Care Provider or designated person (client) can be immediately alerted (as described above). This negative validation can make intervention possible. If the patient does report to class on time, the patient's support network (CP, support network outside of the clinical team) can be notified of his success/accomplishment. This positive reinforcement can encourage communication and outside support.

The event reporting can be possible for every event required through treatment including but not limited to: medication management, curfew check, probation, drug screens, substance abuse treatment, school attendance, client contact. Each and every real-time event occurrence collected through the system replaces the need for the CP to manually log and/or authenticate outputs/outcomes during treatment.

As described herein, the scanning of the QR code can apply to tracking attendance of classes, programs, etc., health management (including behavioral and health treatment), and in home-health, addiction recovery, medication therapy management, behavioral health etc. where the client supports remote patient monitoring. If an event does not happen as scheduled, for example, a negative validation can be logged into the master database 150 (as discussed above) and a designated person (client 130-132) can be immediately alerted via text message (via the transmission of information discussed above).

Figure 2:
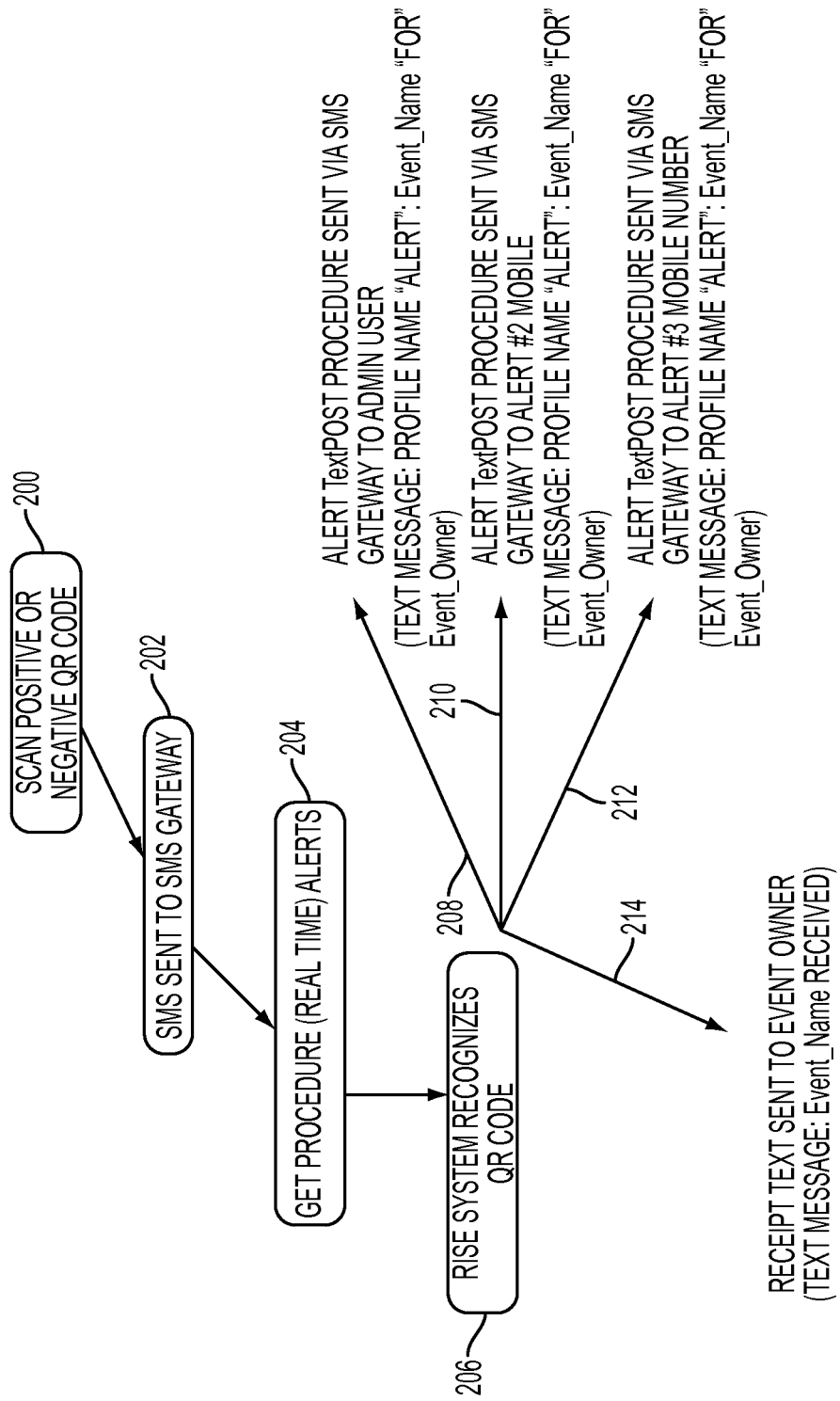
FIG. 2 is a flow chart functional diagram showing certain functionalities of the event based tracking, health management, and patient and treatment monitoring system, according to an embodiment of the present invention.

Turning to FIG. 2, a flow chart functional diagram of certain functionalities of the event based tracking, health management, and patient and treatment monitoring system is shown, according to an embodiment of the present invention. In a first step 200, a positive or negative QR code is scanned by a mobile device configured or programmed to scan the specific QR code. Positive (or affirmative) scans are performed and completed upon the successful completion of a treatment event. Negative (or non-affirmative) scans are performed and completed when a treatment event is specifically not completed (for example, a student does not show up for class). In a second step 202, a SMS text message (for example) is sent to the SMS gateway 116 (as described above with respect to FIG. 1). In a third step 204, procedure (real time) alerts are obtained. In a fourth step 206, the QR code is recognized by the web application preferably running on the master server and database 150 (as discussed above). In a series of next steps the 208-214, the web application is structured and/or programmed to send alerts (e.g., via SMS text) to various designated/approved recipients regarding the scanned QR code data (either positive or negative) and information related thereto.

In particular, step 208 shows that the web application is structured and/or programmed to recognize that a QR code was scanned and instructing the system, i.e., network 100, to ALERT via TEXT POST procedure (after the QR was scanned and info sent to the system and the QR code is verified), that it is sending the results of the QR scan to an authorized client device (e.g., "administrator user's" cell phone via text message (caregiver, doctor, caseworker: health provider)). In step 210, the procedure is similar to step 208, however, the message is being sent to a second authorized person (e.g., "Alert #2" can be a support person, a caregiver of another authorized recipient of a treatment alert text). In step 212, the procedure is similar to step 210, however, the message is being sent to a third authorized person (e.g., "Alert #3" can be a support person, a caregiver of another authorized recipient of a treatment alert text). In step 214, the person who scanned the subject QR code will get a text message from the network 100 confirming the message was sent to the authorized client(s) with the outcome of the scan.

Figure 3:
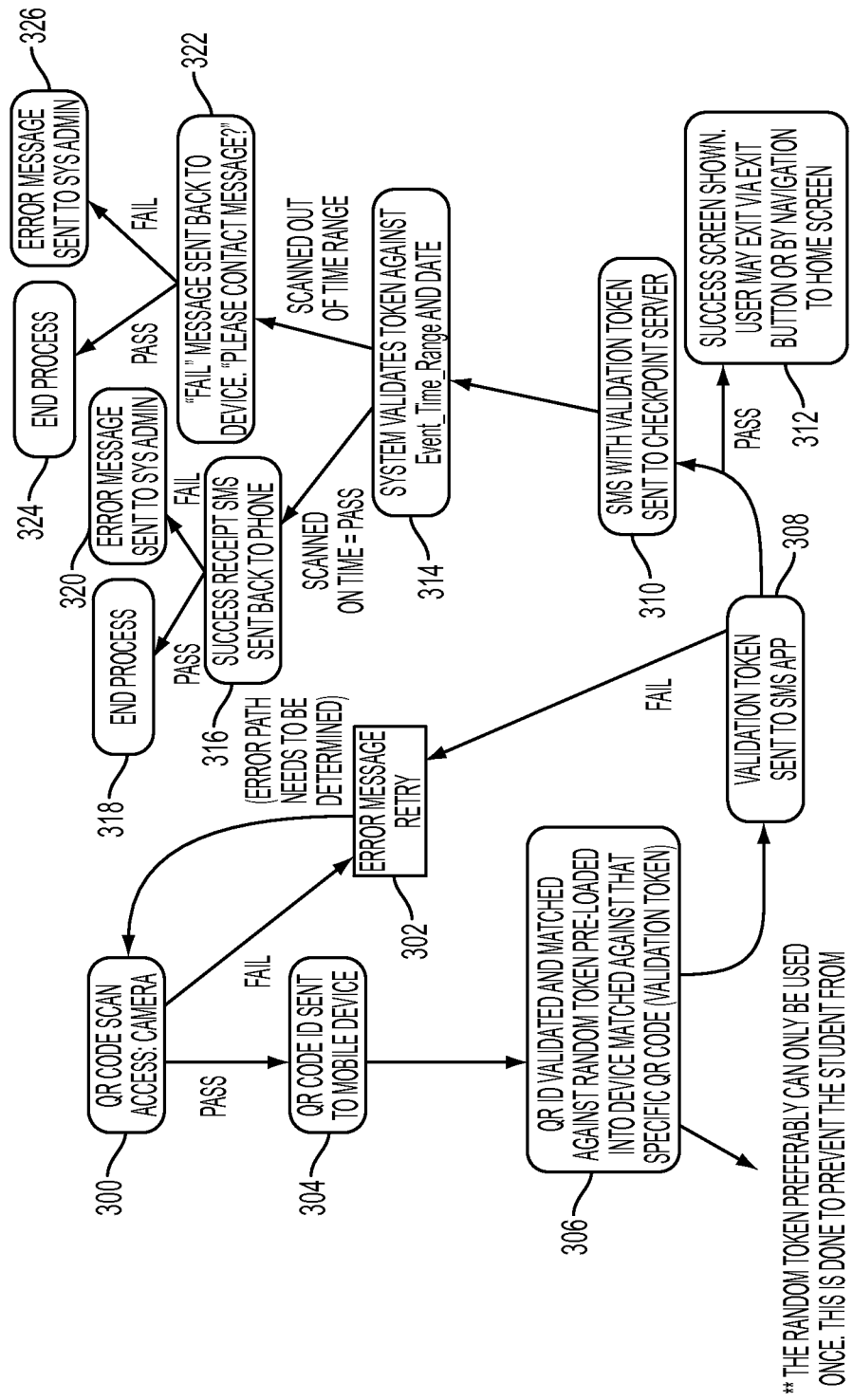
FIG. 3 is a flow chart functional diagram showing an event validation process of the event based tracking, health management, and patient and treatment monitoring system, according to an embodiment of the present invention

Turning to FIG. 3, a flow chart functional diagram of an event validation process of the event based tracking, health management, and patient and treatment monitoring system is shown, according to an embodiment of the present invention. This figure describes how the "back-end system" of an embodiment of the present invention handles a successful or unsuccessful scan of the QR code itself.

In a first step 300, the mobile application of embodiment of the present invention enables a mobile device to scan (through the use of the camera function) a QR code. A "pass" means that the phone (structured or configured to scan the particular QR code per the software application or "mobile app") successfully scanned the QR code and the QR code data and related information was sent from the mobile device to the network 100. A "fail" means that the internal camera in the mobile device or the mobile app stored thereon malfunctioned, and the QR code was not scanned and the information was not sent to the network 100. At which point the mobile app will communicate with the user of the mobile device that the scan us unsuccessful and they need to try again (step 302).

If there is a successful scan, the QR code ID/data is sent to the mobile device at step 304. A validation token is set up within the mobile app to prevent sending false messages or multiple messages of the same event. At step 306, QR code ID/data is validated and matched against a random token pre-loaded into the mobile device. At step 308, the validation token is sent to the web application in network 100. At step 310, the validation token is sent to a network server 150. At step 312, a success screen can be shown to a user. A user may exit the success screen via an Exit button or by navigation back to the home screen. At step 314, the network/system 100 validates the token against Event_Time_Range and Date. If scanned on time and there is a "pass" indication, a success receipt is sent back to the mobile device at step 316, and if successful (a "pass") the process ends at step 318. If there is a fail, an error message can be sent to the system administrator and/or mobile device at step 320. If scanned out of time range, a "fail" message is sent back to the mobile device at step 322. If the "fail" message reaches the mobile device, there is a pass and the process ends at step 324. If the "fail" message fails to reach the mobile device, an error message can be sent to the system administrator and/or mobile device at step 326.

Figure 4:
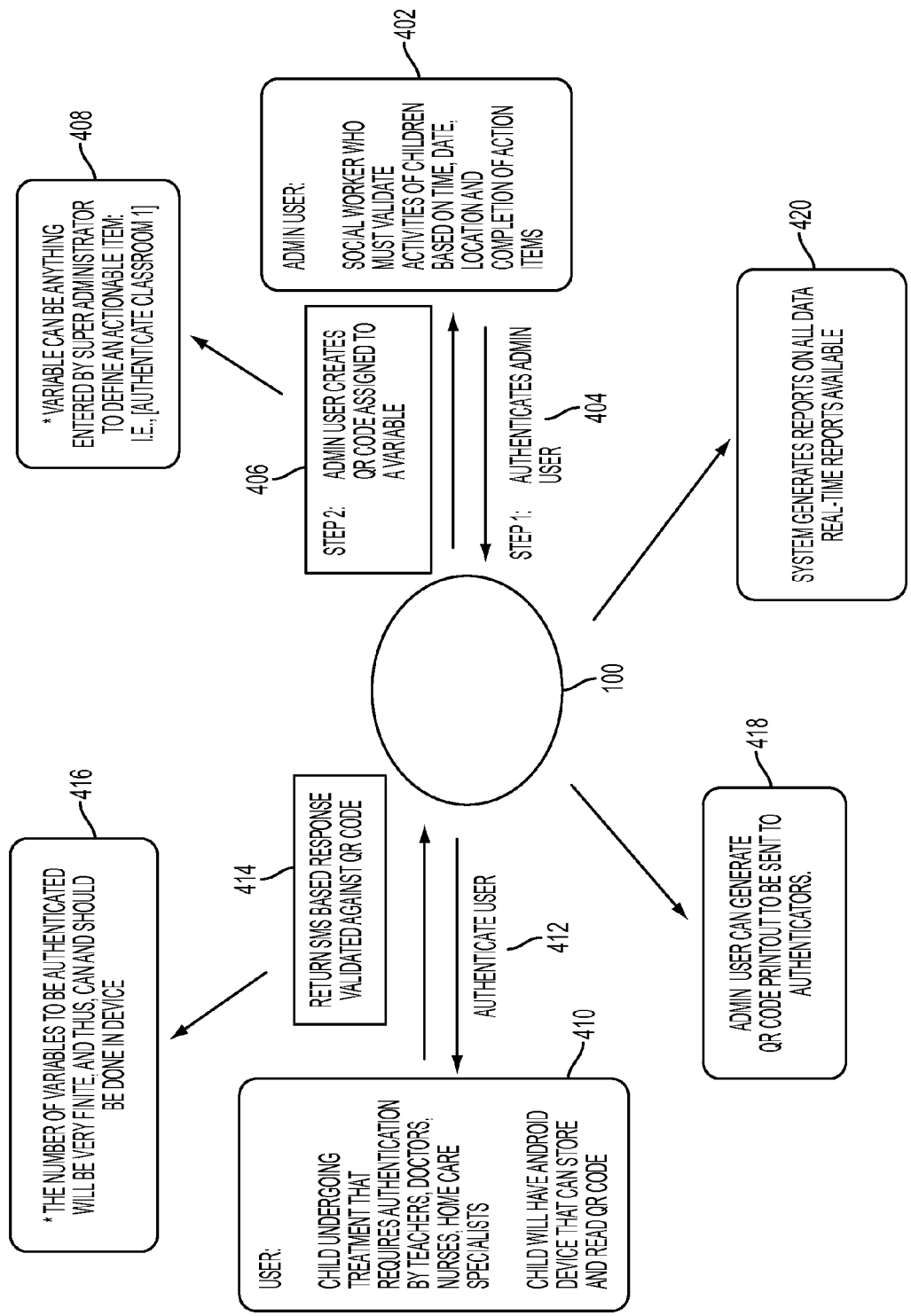
FIG. 4 is a flow chart functional diagram showing certain functionalities/system architecture of the web application of the event based tracking, health management, and patient and treatment monitoring system, according to an embodiment of the present invention.

Turning to FIG. 4, a flow chart functional diagram of certain functionalities/system architecture of the web application of the event based tracking, health management, and patient and treatment monitoring system is shown, according to an embodiment of the present invention. FIG. 4 shows how the "event screens" "look" to the user→java can be the code language→application server supports the web application and stored information into the database/s-. All of these "components" speak with a central node (point of accessing the database) and then the client computer is what the database looks like to the user. The "admin user" in FIG. 4 is typically the person in charge of a treatment plan at issue, and can use these event screens to create QR codes based on a known treatment plan. With respect to FIG. 1, the admin. user can be associated with one of the listed client devices 130-132.

For example, event screen 402 shows information regarding the admin. user, which in this example is a social worker who must validate activities of children based on time, date, location and completion of action items. At step 404, the network system 100 authenticates the admin. user. At step 406, the admin user creates a QR code per use of the network system 100 assigned to a variable. Event screen 408 shows that the variable can be anything entered by a super administrator (or other approved person) to define an actionable item, i.e., [authenticate Classroom 1].

Event screen 410 shows information regarding the "user," which in this example is a child undergoing treatment that requires authentication by teachers, doctors, nurses, and home care specialists, etc. The child can have a mobile device with a mobile app. (as described above) that can store and read the QR code created by the admin. user. At step 412, the network system 100 authenticates the user. At step 414, a return SMS based response validated against the QR code (as described above) is sent from the network system 100. Event screen 416 shows that the number of variables to be authenticated will be very finite, and thus, can and preferably should be done in a user device.

Event screen 418 shows that an admin user can generate a QR code printout to be sent to authenticators. Event screen 420 shows that the network system 100 can generate reports on all data, and that real time reports can be made available.

With respect to FIG. 1, the "user" shown in FIG. 4 can be associated with one of the listed user devices 120-123.

Figure 5A:
Figure 5B:
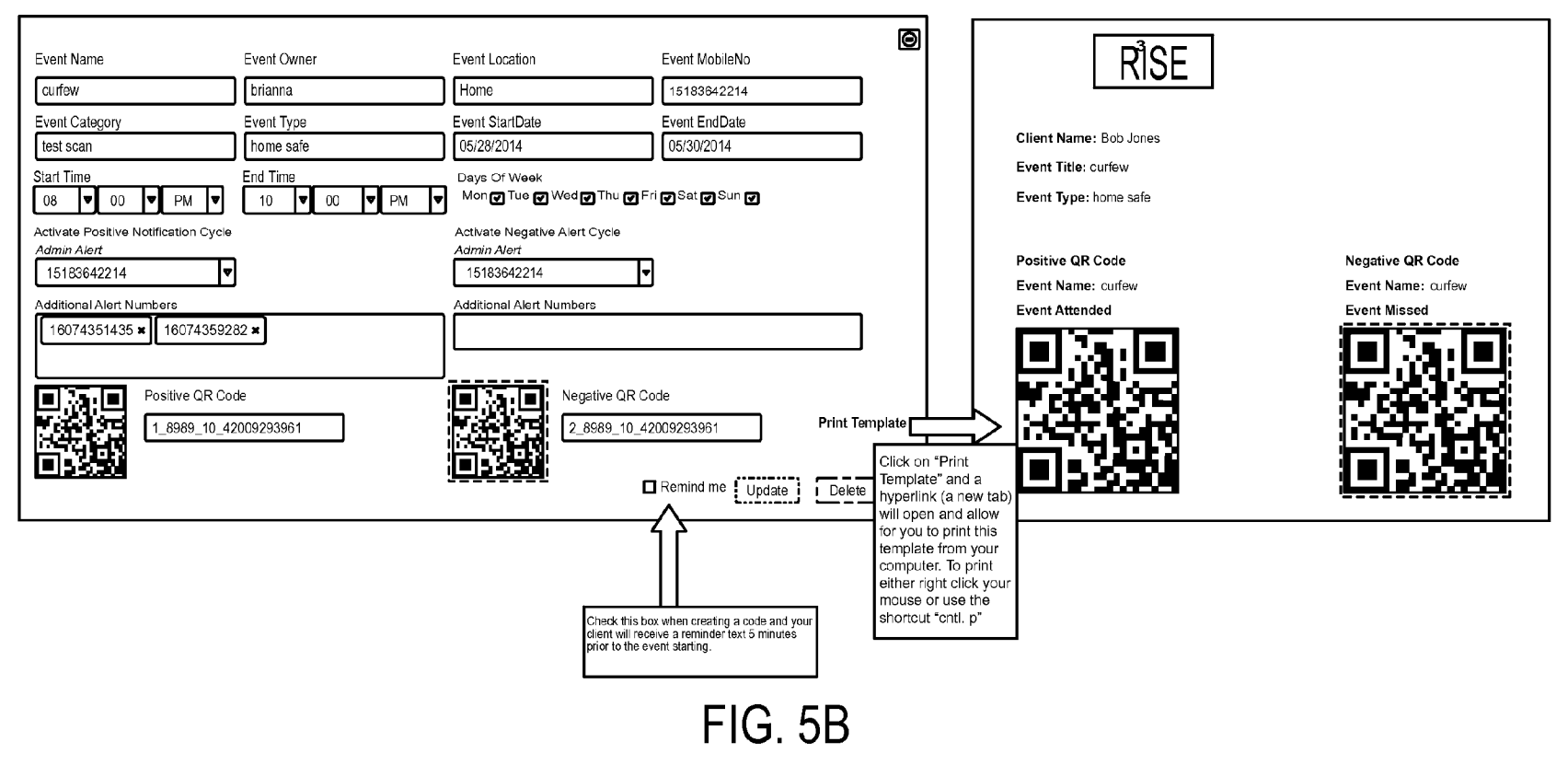
Figure 5C:

Turning to FIGS. 5A-C, an example user interface showing an event and related QR code creation functionality of the event based tracking, health management, and patient and treatment monitoring system is illustrated, according to an embodiment of the present invention. Creating events can be important to the success of automating the recording and reporting of treatment events. Tying these events to the creation of unique customized QR codes that are tied to specific mobile devices can decrease the likelihood of mistakes and/or abuse in the tracking, monitoring, and reporting of these events. In accordance with a preferred embodiment of the present invention, a specialized improved computer is created—here the mobile device—by virtue of it being specifically tied to a unique customized QR code created for a specific positive/negative event (and as a result, programmed to function and interact with a network server etc. in a particular manner as described herein as a result of the mobile device being so tied to the unique customized QR code).

The system of an embodiment of the present invention allows a user (through a web accessible user interface per the web application) to create a client/consumer/patient profile with related client personal and demographic information. Once a client profile has been created, a specific positive/negative event with unique customized positive and negative QR codes can be created and tied to a specific mobile device per the user interface, along with various particulars associated therewith, as will be described further below.

Each of FIGS. 5A-5C shows a web accessible user interface with a template of information, some of which may be necessary for the creation of a particular positive/negative event (FIG. 5A—attendance of a family engagement session, FIG. 5B—meeting of a curfew, and FIG. 5C—taking of a RX 20 mg Oxy) and a unique customized QR code for the particular positive/negative event which is tied to at least one particular mobile device, delivering alerts to mobile devices (as indicated as a tab on this template), compiling reports under a client profile (as indicated as a tab on this template), and setting up time parameters and authentication. These events and related QR codes can be created per interaction with the user interface shown in FIGS. 5A-C, and entry of some or all of the following information under the "Events" tab on the user interface. For example, Event name=title/code of type of treatment event/outcome being tracked; Event Owner=person who is responsible for scanning the QR code; Event Location=place in which the person is completing the event and/or where the scan is going to take place; Event Mobile Number=Phone number of the phone scanning the code*this is for authentication purposes–ONLY the phone number(s) listed here will be able to successfully scan the QR code and have the information sent (i.e., smart phones, tablets and other mobile devices that have downloaded or has access to a mobile app, and are configured or programmed to perform the functionality discussed herein per the downloaded or accessed mobile app); Event Category=general category of the specific event/outcome being tracked (e.g., FIG. 5C "prescription" for the specific Event Name=RX 20 mg of Oxy); Event Type=Specific event information (this is the info sent to the mobile phones); Event Outcomes=Positive: a "positive" QR code is created/generated based on the other entered "event" information, that will send out a message upon being scanned by the particular "tied-to" mobile device that the event was completed successfully; Negative: a "negative" QR code is created/generated based on the other entered "event" information, that will send out a message upon being scanned by the particular "tied-to" mobile device that the event was unsuccessful or not completed; Start Time/End Time and Days of the week—these are time parameters that can be used to track if the event is being completed during the prescribed/necessary time limits. Setting up time parameters is unique, because the system can be configured or programmed to send out a "no scan message" in the case that time ran out and no one scanned a positive OR negative code. This alerts the care provider to check in on the progress of the event. Admin Alter=the phone number of the person who is in charge of care or will be managing the event. Additional Alerts are those persons authorized to receive a text (e.g., a family member, support network person, supervisor, therapist, parole officer etc.).

The positive/negative QR codes can be stored in a particular sub-virtual private servers and databases 151-153, with each code's respective metadata—e.g., indicator of a mobile device tied to the QR codes, patient/consumer/client profile, and event information etc. Any of the fields shown in FIGS. 5A-C can be updated, and thus the positive/negative QR codes can be updated, by changing any of the information in the listed fields and clicking the "update" tab shown in FIGS. 5B-C. New codes can be created by the update, or the new/revised information can be associated with the same positive/negative QR codes. Events and associated QR codes can be deleted by clicking the "delete" tab shown in FIGS. 5B-C.

Turning to the specific example shown in FIG. 5C, the following event to be monitored was created for client/patient/consumer John Doe—RX 20 mg Oxy, a prescription that needs to be taken twice daily during a particular time frame for pain at a clinic starting on Feb. 25, 2014 and ending on Mar. 6, 2014. A positive QR code was created to be scanned representing successful completion of the event (taking of the prescription by John Doe), and a negative QR code was created to be scanned representing non-completion of the event. According to this embodiment of the present invention, each of these unique customized codes are tied to this particular event (and no other event), and can only be scanned by a mobile device with the following mobile device indicator (here, phone number—518-364-2214). Alerts (e.g., of positive, negative, or no scans within the specified date and time) can be sent to the Event Mobile No. and to other mobile device indicators (e.g., phone numbers) as may be necessary or desired (which can be listed as Additional Listed Numbers).

As shown in FIG. 5B, a reminder can be set up by checking the "remind me" box to remind (via text message, email, call, video chat or other communication means) the client/patient/consumer and or the administrator of the event within a certain time frame before the scheduled event. FIG. 5B also shows the creation of a "print template" with the positive and negative QR codes and various metadata regarding the specific positive/negative event, which were created based on the entry of the other "event" information.

Turning back to FIG. 5C, the particular mobile device, which is tied to the positive and negative QR codes (here, the mobile device with the number 518-364-2214), is programmed or configured (via the mobile app) to prompt a login to authenticate the user prior to accessing the mobile app. After login to the mobile app, the app can be opened and the mobile device can be used to scan the positive and/or negative QR code.

Figure 6:
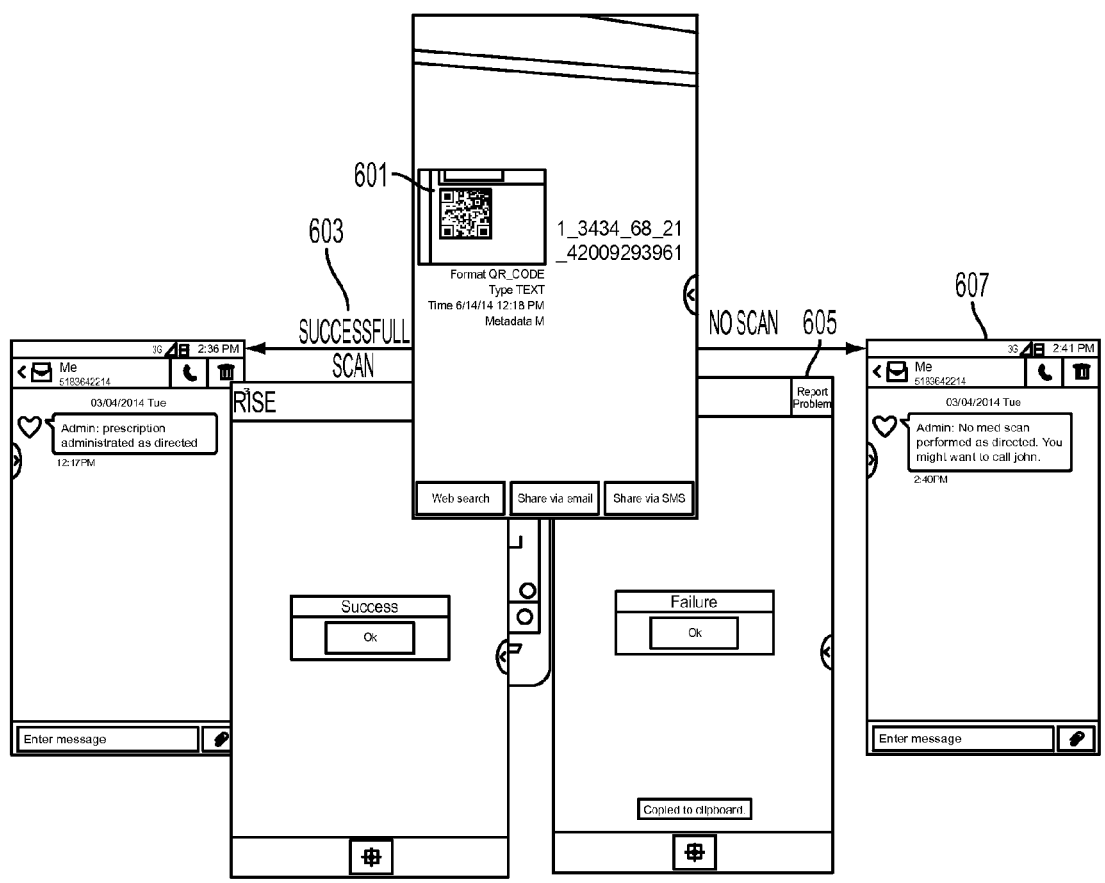
FIG. 6 is an illustration of a successful scan, unsuccessful scan, and no scan within a particular date and time of a positive QR code by a mobile device configured or programmed to so scan per a mobile app and by virtue of the mobile device being tied to the positive QR code, according to an embodiment of the present invention.

Turning to FIG. 6, an illustration is shown of a successful scan 603, unsuccessful scan 605, and no scan 607 within a particular date and time of a positive QR code 601 by the mobile device configured or programmed to so scan etc. per the mobile app and by virtue of the mobile device being tied to the positive QR code (as discussed above), according to an embodiment of the present invention. The mobile device can be configured or programmed to show a success indication (icon or audible sound) upon a successful scan of the positive QR code, and a failure indication (icon or audible sound) upon a failed scan. The system 100 can be configured or programmed to send an alert (e.g., via text) to all authorized mobile devices regarding the update on status (i.e., the successful scan, failure of the scan, or non-scan) upon receipt of QR code scan data from the mobile device or non-receipt of QR code scan data within a predetermined timeframe. The mobile device can be configured to work via WiFi and regular cell signal. If a scan is performed with no communication signal to the mobile device, the mobile device can be configured or programmed to hold the scanned information in batch until the phone is moved into a location with a communication signal—and then the scanned information can be automatically uploaded to the database in system 100. A successful/unsuccessful scan of a negative code can be performed and related alerts and indications can be provided in the same manner, and are not shown here.

Turning to FIG. 7, an illustration of a report that can be generated regarding a series of events and their relative completion indicators and can be provided to clients A-C (130, 131, and 132) or other authorized entities/individuals is shown, according to an embodiment of the present invention. In brief, this report shows whether John Doe successfully completed his event during the dates indicated, i.e., whether he took his prescription on the specified date and within the specified timeframe. The results show that Mr. Doe successfully took his medication on certain dates within the specified timeframe—which are listed as "complete;" took his medication on a specified date but outside the specified timeframe—which are listed as "outside parameters;" and failed to scan or received a negative scan on a specified date—which are listed as "missed." These reports can be available on the specific databases accessable to the clients A-C in real-time. The reports and alerts can be sent to a database (e.g., Quickbase) under an appropriate client profile in batch (e.g., at the end of every day), and are web accessible via logging in to the user interface.

Turning back to FIG. 5C, alerts and reports can also be available through use of web accessible the user interface. The "alerts" tab cab provide a user with a history of all a particular client's QR scan history (including notification if a scan was not performed within a the specified date and timeframe).

A "module," as may be used herein, can include, among other things, the identification of specific functionality represented by specific computer software code of a software program. A software program may contain code representing one or more modules, and the code representing a particular module can be represented by consecutive or non-consecutive lines of code. The computer-executable program instructions of an embodiment of the present invention can comprise any computer-programming language known in the art, including but not limited to C, Java, Python, Perl, ActionScript and JavaScript, among many others.

As will be appreciated by one skilled in the art, aspects of the present invention may be embodied/implemented as a computer system, method or computer program product. The computer program product can have a computer processor or neural network, for example, which carries out the instructions of a computer program. Accordingly, aspects of the present invention may take the form of an entirely hardware embodiment, an entirely software embodiment, and entirely firmware embodiment, or an embodiment combining software/firmware and hardware aspects that may all generally be referred to herein as a "circuit," "module," "system," or an "engine." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, completely or partly on the thermal printer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowcharts/block diagrams in the Figures illustrate the architecture, functionality, and operation of possible implementations of systems, methods, and computer program products according to various embodiments of the present invention. In this regard, each block in the flowcharts/block diagrams may represent a module, segment, or portion of code, which comprises instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While several embodiments of the invention have been discussed, it will be appreciated by those skilled in the art that various modifications and variations of the present invention are possible. Such modifications do not depart from the spirit and scope of the present invention.

What is claimed is:

1. A computer implemented method for associating a unique scannable code with a positive/negative event and a unique mobile device, the method comprising:
   creating at least a first unique scannable code and at least a second unique scannable code;
   associating said at least a first unique scannable code with successful completion of a positive/negative event;
   associating said at least a second unique scannable code with noncompletion of the positive/negative event;
   associating said at least a first unique scannable code and said at least a second unique scannable code with said mobile device, wherein said mobile device is configured or programmed to scan one of said at least a first unique scannable code or at least a second unique scannable code.

2. The method of claim 1, further comprising the step of associating said at least a second unique scannable code with said mobile device, wherein said mobile device is configured or programmed to scan said at least a second unique scannable code.

3. The method of claim 1, wherein said unique scannable code further comprises a quick response code.

4. The method of claim 1, wherein said positive/negative event further comprises an event selected from the group consisting of medical treatment, medication intake, attendance, curfew, probation check in, drug screen, and substance abuse treatment.

5. A computer implemented method for scanning and processing a unique scannable code associated with a positive/negative event and a unique mobile device, the method comprising:
providing at least a first unique scannable code, wherein said at least a first unique scannable code is a positive code associated with successful completion of a positive/negative event,
providing a unique mobile device, wherein said mobile device is associated with said at least a first unique scannable code and is configured or programmed to scan said at least a first unique scannable code;
scanning said positive code with said mobile device upon successful completion of the positive/negative event;
checking a time said positive code was scanned to determine whether the successful completion of the positive/negative event occurred within a timeframe said positive/negative event was scheduled to occur.

6. The method of claim 5, further comprising a step of validating a successful scan of said positive code by said mobile device by matching the scanned positive code with a validation token associated with said positive code and stored within said mobile device.

7. The method of claim 6, further comprising a step of transmitting said validation token by said mobile device to a network server.

8. The method of claim 7, further comprising the step of logging, by said network server, a positive validation when said validation token indicates that the positive code was scanned within predetermined event parameters, wherein said predetermined event parameters comprise a particular date and timeframe within which said positive/negative event was scheduled to occur.

9. The method of claim 8, further comprising a step of transmitting, by said network server, real time alerts to designated computer devices regarding said successful scan of said positive code by said mobile device.

10. The method of claim 5, further comprising providing a second unique scannable code, wherein said second unique scannable code is a negative code associated with non-completion of a positive/negative event, and wherein said mobile device is associated with said second unique scannable code and is configured or programmed to scan said second unique scannable code.

11. The method of claim 10, further comprising the step of scanning said negative code with said mobile device upon non-completion of the positive/negative event.

12. The method of claim 10, further comprising a step of validating a successful scan of said negative code by said mobile device by matching the scanned negative code with a validation token associated with said negative code and stored within said mobile device and transmitting said validation code by said mobile device to the network server.

13. The method of claim 12, further comprising a step of logging, by said network server, a negative validation when said validation token indicates that the negative code was scanned outside of predetermined event parameters, wherein said predetermined event parameters comprise a particular date and timeframe within which said positive/negative event was scheduled to occur.

14. The method of claim 10, further comprising a step of transmitting, by said network server, real time alerts to designated computer devices regarding said successful scan of said negative code by said mobile device.

15. An event based tracking, health management, and patient and treatment monitoring system comprising:
a unique mobile device, wherein said mobile device is associated with at least a first unique scannable code associated with the successful completion of a positive/negative event, and at least a second unique scannable code associated with the non-completion of the positive/negative event and is configured or programmed to scan said at least the first unique scannable code;
a network server in communication with said mobile device, wherein:
said mobile device is further configured to transmit data regarding a successful scan by said mobile device of said at least a first unique scannable code to said network server; and
said network server configured to store said data regarding the successful scan of said at least a first unique scannable code, and to transmit real time alerts to designated computer devices regarding said data.

16. An event based tracking, health management, and patient and treatment monitoring system comprising:
a unique mobile device, wherein said mobile device is associated with at least a first unique scannable code associated with positive/negative event, and is configured or programmed to scan said at least the first unique scannable code;
a network server in communication with said mobile device, wherein:
said mobile device is further configured to transmit data regarding a successful scan by said mobile device of said at least a first unique scannable code to said network server; and
said network server configured to store said data regarding the successful scan of said at least a first unique scannable code, and to check a time said scannable code was scanned to determine whether the successful completion of the positive/negative event occurred within a timeframe said positive/negative event was scheduled to occur, and to transmit real time alerts to designated computer devices regarding said data.

* * * * *